US009791399B2

(12) United States Patent
McGuinness et al.

(10) Patent No.: US 9,791,399 B2
(45) Date of Patent: Oct. 17, 2017

(54) DERIVATIZATION OF CARBON (71) Applicant: SCHLUMBERGER TECHNOLOGY CORPORATION, Sugar Land, TX (US)

(72) Inventors: Kay McGuinness, Milton (GB); Nathan Lawrence, Wyton (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 295 days.

(21) Appl. No.: 14/365,623

(22) PCT Filed: Dec. 21, 2012

(86) PCT No.: PCT/IB2012/057616
§ 371 (c)(1),
(2) Date: Jun. 14, 2014

(87) PCT Pub. No.: WO2013/093882
PCT Pub. Date: Jun. 27, 2013

(65) Prior Publication Data
US 2014/0332412 A1    Nov. 13, 2014

(30) Foreign Application Priority Data
Dec. 21, 2011   (GB) .................................. 1122058.9

(51) Int. Cl.
*G01N 27/30*   (2006.01)
*C01B 31/02*   (2006.01)
(Continued)

(52) U.S. Cl.
CPC ............ *G01N 27/302* (2013.01); *B82Y 30/00* (2013.01); *B82Y 40/00* (2013.01);
(Continued)

(58) Field of Classification Search
CPC .................................................... G01N 27/302
See application file for complete search history.

(56) References Cited

U.S. PATENT DOCUMENTS 3,780,575 A    12/1973   Urbanosky
3,859,851 A    1/1975    Urbanosky
(Continued)

FOREIGN PATENT DOCUMENTS

CN    101870467 B    12/2011
GB      2409902 B     4/2006
(Continued)

OTHER PUBLICATIONS

Bahr, el al., "Functionalization of Carbon Nanotubes by Electrochemical Reduction of Aryl Diazonium Salts: A Bucky Paper Electrode", 2001, Journal of the American Chemical Society, vol. 123, pp. 6536-6542.*
(Continued)

*Primary Examiner* — Jill Warden
*Assistant Examiner* — Matthew Krcha (57) ABSTRACT Chemical modification of the surface of elemental carbon comprises a first stage of attaching a compound with an azo group to the elemental carbon and then a second stage of decomposing the azo group in the presence of one or more compounds with an olefinic group so that decomposition of the azo group forms radicals attached to the carbon surface and a said radical forms a covalent bond to a said olefinic group. The second stage may proceed as a polymerization of a vinyl monomer with a redox active group such as ferrocene, anthracene or anthraquinone. The resulting polymer-modified carbon may be used in an electrochemical sensor.

8 Claims, 3 Drawing Sheets (51) Int. Cl.

| | |
|---|---|
| C01B 31/04 | (2006.01) |
| C09C 1/44 | (2006.01) |
| B82Y 30/00 | (2011.01) |
| B82Y 40/00 | (2011.01) |
| C07F 15/02 | (2006.01) |

(52) U.S. Cl.
CPC .......... *C01B 31/0273* (2013.01); *C01B 31/04* (2013.01); *C01B 31/0484* (2013.01); *C07F 15/02* (2013.01); *C09C 1/44* (2013.01)

(56) References Cited

U.S. PATENT DOCUMENTS

| | | | |
|---|---|---|---|
| 4,648,478 | A | 3/1987 | Dedole et al. |
| 4,702,343 | A | 10/1987 | Paulsson |
| 4,932,003 | A | 6/1990 | Winbow et al. |
| 4,994,671 | A | 2/1991 | Safinya et al. |
| 5,115,880 | A | 5/1992 | Sallas et al. |
| 5,159,160 | A | 10/1992 | Brett |
| 5,229,554 | A | 7/1993 | Cole |
| 5,309,405 | A | 5/1994 | Brett et al. |
| 5,893,383 | A | 4/1999 | Facteau |
| 6,015,010 | A | 1/2000 | Kostrov |
| 6,059,031 | A | 5/2000 | Brett |
| 6,179,084 | B1 | 1/2001 | Yamamoto et al. |
| 6,247,533 | B1 | 6/2001 | Brett |
| 6,550,534 | B2 | 4/2003 | Brett |
| 6,905,667 | B1 | 6/2005 | Chen et al. |
| 7,125,533 | B2 | 10/2006 | Khabashesku et al. |
| 7,182,170 | B1 | 2/2007 | Brett et al. |
| 2004/0222081 | A1 | 11/2004 | Tour et al. |
| 2005/0147553 | A1 | 7/2005 | Wong et al. |
| 2007/0280876 | A1 | 12/2007 | Tour et al. |
| 2009/0178921 | A1 | 7/2009 | Lawrence et al. |
| 2009/0301896 | A1 | 12/2009 | Tour et al. |
| 2011/0094732 | A1 | 4/2011 | Lehman et al. |

FOREIGN PATENT DOCUMENTS

| | | | |
|---|---|---|---|
| WO | 0140623 | A1 | 6/2001 |
| WO | 2004063743 | A1 | 7/2004 |
| WO | 2005066618 | A1 | 7/2005 |
| WO | 2010001082 | A1 | 1/2010 |
| WO | 2010106404 | A2 | 9/2010 |

OTHER PUBLICATIONS

Hayes, et al., "Preservation of NADH Voltammetry for Enzyme-Modified Electrodes Based on Dehydrogenase," Anal. Chem., vol. 71, 1999, pp. 1720-1727.
Allongue, et al., "Covalent Modification of Carbon Surfaces by Aryl Radicals Generated from the Electrochemical Reduction of Diazonium Salts", 1997, Journal of the American Chemical Society, vol. 119, No. 1, pp. 201-207.
Andrieux, et al., "Derivatization of Carbon Surfaces by Anodic Oxidation of Arylacetates: Electrochemical Manipulation of the Grafted Films", 1997, Journal of the American Chemical Society, vol. 119, No. 18, pp. 4292-4300.
Antoniadou, et al., "Anion exchange activity of electrochemically bonded ethylene diamine on carbon fibres", 1992, Journal of Applied Electrochemistry, vol. 22, pp. 1060-1064.
Aso, et al., "Cationic polymerization and copolymerization of vinylferrocene", May 22, 1969, Macromolecular Chemistry and Physics, vol. 124, Issue 1, pp. 232-240.
Baker, et al., "Covalently Bonded Adducts of Deoxyribonucleic Acid (DNA) Oligonucleotides with Single-Wall Carbon Nanotubes: Synthesis and Hybridization", 2002, Nano Letters, vol. 2, No. 12, pp. 1413-1417.
Barbier, et al., "Electrochemical Bonding of Amines to Carbon Fiber Surfaces Toward Improved CarbonEpoxy Composites", 1990, Journal of The Electrochemical Society, vol. 137, No. 6, pp. 1757-1764.
Baughman, et al., "Carbon nanotube actuators", May 1999, Science, vol. 284, No. 5418, pp. 1340-1344.
Baumert, et al., "Styrene-vinylferrocene random and block copolymers by TEMPO-mediated radical polymerization", Apr. 1999, Macromolecular Rapid Communications, vol. 20, Issue 4, pp. 203-209.
Calvert, "Nanotube composites: A recipe for strength", May 20, 1999, Nature, vol. 399, No. 6733, p. 210.
Campidelli, et al., "Dendritic liquid—crystalline fullerene-ferrocene dyads", Feb. 27, 2006, Tetrahedron, vol. 62, Issue 9, Supramolecular Chemistry of Fullerenes, pp. 2115-2122.
Casado, et al., "Siloxane and Organosilicon Dimers, Monomers, and Polymers with Amide-Linked Ferrocenyl Moieties. Synthesis, Characterization, and Redox Properties", 1995, Inorganic Chemistry, vol. 34, No. 7, pp. 1668-1680.
Che, et al., "Carbon nanotubule membranes for electrochemical energy storage and production", May 28, 1998, Nature, vol. 393, No. 6683, pp. 346-348.
Cochet, et al., "Synthesis of a new polyaniline/anotube composite: "in-situ" polymerisation and charge transfer through site-selective interaction", 2001, Chemical Communications, vol. 16, pp. 1450-1451.
Collins, et al., "Nanotube Nanodevice", Oct. 3, 1997, Science, vol. 278, pp. 100-102.
De Andrade, "Dynamic and Static Fluorescence Spectroscopy Applied to Miscibility of Poly(n-butyl methacrylate-co-styrene) with Polystyrene and Morphological Analysis by Epifluorescence Microscopy", 2004, The Journal of Physical Chemistry B, vol. 108, No. 13, pp. 3975-3984.
De Heer, et al., "A Carbon Nanotube Field-Emission Electron Source", Nov. 17, 1995, Science, vol. 270, pp. 1179-1180.
Deinhammer, et al., "Electrochemical Oxidation of Amine-Containing Compounds: a route to the surface modification of glassy carbon electrodes", 1994, Langmuir, vol. 10, No. 4, pp. 1306-1313.
Downard, "Electrochemically Assisted Covalent Modification of Carbon Electrodes", Feb. 29, 2000, Electroanaysis, vol. 12, No. 14, pp. 1085-1096.
Fan, et al., "Synthesis, characterizations, and physical properties of carbon nanotubes coated by conducting polypyrrole", Dec. 9, 1999, Journal of Applied Polymer Science, vol. 74, No. 11, pp. 2605-2610.
Gonsalves, et al., "Ferrocene-containing polyamides and polyureas", 1984, Journal of the American Chemical Society, vol. 106, No. 13, pp. 3862-3863.
Iijima, et al., "Single-shell carbon nanotubes of 1-nm diameter", Jun. 17, 1993, Nature, vol. 363, No. 6430, pp. 603-605.
Katz, "Polymerization and copolymerization of 1- and 9-vinylanthracenes and 9-vinylphenanthrene", May 1963, Journal of Polymer Science Part A: General Papers, vol. 1, Issue 5, pp. 1635-1643.
Kong, et al., "Controlled Functionalization of Multiwalled Carbon Nanotubes by in Situ Atom Transfer Radical Polymerization", Jan. 21, 2004, Journal of the American Chemical Society, vol. 126, No. 2, pp. 412-413.
Krakovyak, et al., "Investigation of polymerization and copolymerization of 9-vinyl-anthracenes", Aug. 1974, European Polymer Journal, vol. 10, Issue 8, pp. 685-692.
Kroto, et al., "C60: Buckminsterfullerene", Nov. 14, 1985, Nature, vol. 318, pp. 162-163.
Kuramoto, et al., "Thermosensitive and redox-active polymers: Preparation and properties of poly(N-ethylacrylamide-co-vinylferrocene) and poly(N,N-diethylacrylamide-co-vinylferrocene)", Jul. 30, 1997, Journal of Polymer Science Part A: Polymer Chemistry, vol. 35, Issue 10, pp. 1967-1972.
Lai, et al., "Free-radical homopolymerization and copolymerization of vinylferrocene", Mar. 1971, Journal of Polymer Science Part A-1: Polymer Chemistry, vol. 9, Issue 3, pp. 651-662.
Lawrence, "Amperometric Detection of Sulfide: An Electrocatalytic Reaction with Ferrocene Carboxylate", Sep. 2006, Electroanalysis, vol. 18, Issue 17, pp. 1658-1663.
Leventis, et al., "Derivatised carbon powder electrodes: reagentless pH sensors", Jul. 8, 2004, Talanta, vol. 63, No. 4, pp. 1039-1051.
Liu, et al., "Fullerene Pipes", May 22, 1998, Science, vol. 280, pp. 1253-1256.

(56) References Cited

OTHER PUBLICATIONS

Liu, et al., "Preparing a Styrenic Polymer Composite Containing Well-Dispersed Carbon Nanotubes: Anionic Polymerization of a Nanotube-Bound p-Methylstyrene", 2004, Macromolecules, vol. 37, No. 2, pp. 283-287.
McCarthy, et al., "Microscopy studies of nanotube-conjugated polymer interactions", Mar. 15, 2001, Synthetic Metals, vol. 121, pp. 1225-1226.
Mihai, et al., "Poly(ferrocenylenevinylene) from Ring-Opening Metathesis Polymerization of ansa-(Vinylene)ferrocene", 1997, Organometallics, vol. 16, No. 7, pp. 1507-1510.
Modi, et al., "Miniaturized gas ionization sensors using carbon nanotubes", Jul. 10, 2003, Letters to Nature, Nature, vol. 424, pp. 171-174.
Nelson, et al., "Thermal Ring-Opening Polymerization of Hydrocarbon-Bridged [2]Ferrocenophanes: Synthesis and Properties of Poly(ferrocenylethylene)s and Their Charge-Transfer Polymer Salts with Tetracyanoethylene", Apr. 1997, Chemistry—A European Journal, vol. 3, No. 4, pp. 573-584.
Nuyken, et al., "Anionic homo- and block copolymerization of vinylferrocene", Nov. 1997, Macromolecular Chemistry and Physics, vol. 198, Issue 11, pp. 3353-3363.
Nuyken, et al., "Novel sulfur-containing ferrocene polymers", Oct. 1996, Macromolecular Chemistry and Physics, vol. 197, Issue 10, pp. 3343-3354.
O'Connell, et al., "Reversible water-solubilization of single-walled carbon nanotubes by polymer wrapping", Jul. 13, 2001, Chemical Physics Letters, vol. 342, Issues 3-4, pp. 265-271.
Pan, et al., "Very long carbon nanotubes", Aug. 13, 1998, Nature, vol. 394, No. 6694, pp. 631-632.
Pandurangappa, et al., "Homogeneous chemical derivatisation of carbon particles: a novel method for functionalising carbon surfaces", 2002, Analyst, vol. 127, No. 12, pp. 1568-1571.
Pandurangappa, et al., "Physical adsorption of N,N'-diphenyl-p-phenylenediamine onto carbon particles: Application to the detection of sulfide", 2003, Analyst, vol. 128, pp. 473-479.
Qin, et al., "Polymer Brushes on Single-Walled Carbon Nanotubes by Atom Transfer Radical Polymerization of n-Butyl Methacrylate", Dec. 10, 2003, Journal of the American Chemical Society, vol. 126, No. 1, pp. 170-176.
Rabjohns, et al., "Synthesis of aromatic polyamides containing anthracene units via a precursor polymer approach", 1997, Polymer, vol. 38, No. 13, pp. 3395-3407.
Riggs, et al., "Optical Limiting Properties of Suspended and Solubilized Carbon Nanotubes", 2000, The Journal of Physical Chemistry B, vol. 104, No. 30, pp. 7071-7076.
Sadowska, et al., "Synthesis, characterization, and electrochemical testing of carbon nanotubes derivatized with azobenzene and anthraquinone", May 2009, Carbon, vol. 47, Issue 6, pp. 1501-1510.
Perng, et al., "Studies on the mesomorphic properties of ferrocenylene-based organophosphorous liquid-crystalline polymers containing phenyl and biphenyl pendant units", May 14, 2002, Journal of Applied Polymer Science, vol. 85, Issue 4, pp. 831-841.
Švancara, et al., "Carbon Paste Electrodes in Modern Electroanalysis", 2001, Critical Reviews in Analytical Chemistry, vol. 31, Issue 4, pp. 311-345.
Takeuchi, et al., "Accelerated free-radical copolymerization of 9-vinylanthracene with methyl methacrylate using ethylaluminium sesquichloride", Dec. 1989, Macromolecular Chemistry and Physics, Rapid Communications, vol. 10, Issue 12, pp. 645-648.
Tiera, et al., "Fluorescence study of the interaction between metal ions and methyl methacrylate—methacrylic acid copolymers in aqueous solutions: thallium(I), calcium(II), and terbium(III)", Mar. 1998, Colloid and Polymer Science, vol. 276, Issue 3, pp. 206-212.
Turrin, et al., "Behavior of an Optically Active Ferrocene Chiral Shell Located within Phosphorus-Containing Dendrimers", 2002, Organometallics, vol. 21, No. 9, pp. 1891-1897.
Allongue et al, "Covalent Modification of Carbon Surfaces by Aryl Radicals Generated from the Electrochemical Reduction of Diazonium Salts," J. Am. Chem. Soc. vol. 119, pp. 201-207 (1997).
Delamar et al, "Modification of Carbon Fiber Surfaces by Electrochemical Reduction of Aryl Diazonium alts: Application to Carbon Epoxy Composites", Carbon vol. 35, pp. 801-807 (1997).
Ortiz et al, "Electrochemical Modification of a Carbon Electrode Using Aromatic Diazonium Salts. 2. Electrochemistry of 4-nitrophenyl Modified Glassy Carbon Electrodes in Aqueous Media," J. Electroanalytical Chemistry vol. 455 pp. 75-81 (1998).
Saby et al, "Electrochemical Modification of Glassy Carbon Electrode Using Aromatic Diazonium Salts. 1. Blocking Effect of 4-Nitrophenyl and 4-Carboxyphenyl Groups," Langmuir vol. 13, pp. 6805-6813 (1997).
Delamar et al, "Covalent Modification of Carbon Surfaces by Grafting of Functionalized Aryl Radicals Produced from Electrochemical Reduction of Diazonium Salts," J. Am. Chem. Soc. vol. 114, pp. 5883-5884 (1992).
Viswanathan, et al., "Single-Step in Situ Synthesis of Polymer-Grafted Single-Wall Nanotube Composites", Journal of the American Chemical Society, vol. 125, No. 31, 2003, pp. 9258-9259.
Wildgoose, G. et al., "Anthraquinone-derivatised carbon powder: reagentless voltammetric pH electrodes", Talanta, vol. 60, No. 5, Jul. 27, 2003, pp. 887-893
Wright, et al., "Organometallic Nonlinear Optical Polymers. 4. Organometallic Main-Chain, Side-Chain, and Guest-Host Polymers: A Study of Their Orientation and Relaxation Using Second Harmonic Generation", Macromolecules, vol. 27, No. 11, 1994, pp. 3016-3022.
Yang, et al., "Novel Synthesis and Characterization of Side-Chain Ferrocene-Containing Polymers", Macromolecules, 2002, vol. 35, No. 9, 2002, pp. 3426-3432.
Yao, et al., "Polymerization from the Surface of Single-Walled Carbon Nanotubes Preparation and Characterization of Nanocomposites", Journal of the American Chemical Society, vol. 125, Issue 51, Dec. 2, 2003, pp. 16015-16024.
Zhang, et al., "9-(Guanidinomethyl)-10-vinylanthracene: a suitable fluorescent monomer for MIPs", Tetrahedron Letters, vol. 42, Issue 26, Jun. 25, 2001, pp. 4413-4416.
Zhou, et al., "Functionalized Single Wall Carbon Nanotubes Treated with Pyrrole for Electrochemical Supercapacitor Membranes", Chemistry of Materials, vol. 17, No. 8, 2005, pp. 1997-2002.
Robinson, et al., "A Vinylanthracene and Vinylferrocene-Containing Copolymer: A New Dual pH/Sulfide Sensor", Wiley-VCH InterScience, Electroanalysis, (2006) pp. 678-683.
Robinson, et al., "Sulfide Sensing Via Differential Counter ion Diffusion rates Through Redox-Modulated Poly (Vinylferrocene) Microparticles", Electrochemistry Communications, vol. 8, (2006) pp. 1055-1061.
Robinson, et al., "Redox-Sensitive Copolymer: A Single-Component pH Sensor", Anal. Chem. (2006), vol. 78, pp. 2450-2455.
Moniruzzaman, et al., "Tuning the Mechanical Properties of SWNT/Nylon 6,10 Composites with the Flexible Spacers to Intervace", American Chem. Soc., Nano Letters, vol. 7, (2007) pp, 1178-1185.
Guo, et al., "Modification of a Glassy Carbon Electrode with Diols for the Suppression of Electrode Fouling in Biological Fluids", Chem. Pharm. Bull., vol. 44, (1996) pp. 860-862.
Holzinger, et al., "Sidewall Functionalization of Carbon Nanotubes", Angew. Chem. Int. Ed., vol. 40 (2001) pp. 4002-4005.
Lawrence, et al., "Selective Determination of Thiols: A Novel Electroanalytical Approach", Analyst, vol. 125, vol. 125 pp. 661-663,.
Adams, et al., "Preparation and Characterization of Sulfonic Acid-Functionalized Single-Walled Carbon Nanotubes", Phisica E, vol. 41 (2009) pp. 723-728.
Jeroschewski, et al., "Galvanic Sensor for Determination of Hydrogen Sulfide", Electroanalysis, vol., 6 (1994) pp. 769-772.
Ye, et al., "Electrocatalytic O2 Reduction at Glassy Carbon Electrodes Modified with Dendrimer-Encapsulated Pt Nanoparticles", J. Am. Chem. Soc., vol. 127, pp. 4930-4934.

* cited by examiner

DERIVATIZATION OF CARBON

BACKGROUND

Derivatization of carbon surfaces, i.e. the covalent attachment of molecules to the surface of elemental carbon, has attracted considerable interest in recent years, in particular in connection with attaching molecules to carbon nanotubes.

The derivatization of carbon may be carried out for a range of purposes which include modification of the surface properties of a carbon substrate, preparation of carbon-epoxy composites and attaching a molecule to a carbon electrode so that it can take part in an electrochemical reaction in an electrochemical sensor or an electrochemical catalyst.

Traditionally, carbon surfaces were modified by vigorous oxidation on the surface leading to the formation of carboxylic, quinonic, ketonic or hydroxylic groups, which were then reacted further with the target molecule.

A number of procedures have been described for electrochemical induced derivatization leading to the formation of a single covalent bond between a carbon electrode and a moiety which becomes attached. Examples have included electro-oxidation of primary and secondary amines described by Barbier et al J. Electrochem. Soc., vol 137, page 135 (1990), Antoniadou et al J. Appl. Electrochem., 1992, vol 22, page 1060 (1992) and Deinhammer et al Langmuir vol 10 page 1306 1994); electro-oxidation of carboxylates described by C. P. Andrieux et al, J. Am. Chem. Soc., vol 119, page 4292 (1997); and electro-reduction of diazonium salts described by P. Allongue et al J. Am. Chem. Soc., vol 119, page 201 (1997).

There have also been a number of disclosures of routes for derivatization of carbon, without electrochemistry. These include the homogeneous reduction of diazonium compounds in reducing media as described by Pandurangappa et al Analyst, vol 127, page 1568 (2002) and Leventis et al, Talanta vol 63, page 1039 (2004). Also in this category is WO2005/066618 (Schlumberger) which includes description of the diazocoupling of anthraquinonyl and nitrophenyl groups onto carbon nanotubes by means of the reduction of diazonium salts. WO2010/106404 teaches exposing the carbon to a reaction mixture in which a reactive carbene is transiently formed by reaction between a precursor and an extremely strong base.

SUMMARY

This summary is provided to introduce a selection of concepts that are further described below. This summary is not intended to be used as an aid in limiting the scope of the subject matter claimed.

A first aspect of the subject matter disclosed by this application provides a process for chemical modification of the surface of elemental carbon comprising attaching a compound with an azo group to the elemental carbon and then decomposing the azo group in the presence of one or more compounds with an olefinic group so that decomposition of the azo group forms radicals attached to the carbon surface and a said radical forms a covalent bond to a said olefinic group.

When the azo compound is decomposed, two radicals are formed. One of these radicals is attached to the carbon surface. Reaction of a radical with an olefinic group forms a bond, generally a carbon-carbon bond, to one atom of the olefinic group.

The immediate product of such a reaction will also be a radical. Consequently, the reaction may proceed as a polymerisation in which the compound with an olefinic group or a mixture of compounds with olefinic groups, are the monomer(s) which become converted to a polymer chain attached to the carbon surface. These monomers may be vinyl compounds and more specifically may be one or more aromatic compounds with a vinyl group attached to an aromatic ring. It is also possible that a compound containing an olefinic group will be attacked by the radical on the carbon surface but polymer chain formation will terminate instead of propagating.

The azo compound which is decomposed to radicals may be attached directly to the elemental carbon surface. This can be done with an azo compound which also has a diazonium group attached to it. The diazonium group is reduced in the presence of the elemental carbon in accordance with the known procedure for derivatisation of carbon with a diazonium compound.

Another possibility is to begin by derivatizing the elemental carbon with a functional group which does not contain an azo group and then react this group with an azo compound. For instance, this may be accomplished using the known process for treating elemental carbon with a strong oxidising acid to introduce carboxylic acid groups attached to carbon which can be utilised for attachment of another compound.

In embodiments, the olefinic compound(s) may introduce one or more moieties which can undergo redox reactions and can be used in an electrochemical sensor. The present disclosure includes carbon which has been derivatized by the process above, and products which incorporate such derivatized carbon.

So another aspect of the subject matter disclosed herein provides an electrochemical sensor electrode comprising elemental carbon having one or more redox-active compounds attached thereto by the process above. Such a sensor may be a constituent part of measuring apparatus which also has means to apply voltage to the electrode and measure current flow.

Such apparatus may be used for determining presence or concentration of an analyte, and a further aspect of the subject matter disclosed herein provides a method of determining presence or concentration of an analyte in a liquid, comprising contacting the liquid with at least two electrodes, at least one of which is an electrode comprising elemental carbon having a redox-active group covalently attached thereto through a process as above and carrying out electrochemical measurement with the electrodes. The liquid which contains the analyte may be an aqueous solution but it may also be a non-aqueous liquid such as acetonitrile. A method of determining analyte concentration may comprise applying a potential to the sensor electrode(s) in a sweep over a range sufficient to bring about at least one oxidation and/or reduction of the redox active compound; measuring potential or potentials corresponding to one or more said oxidation and/or reductions; and then processing the measurements to give a determination of analyte concentration.

Within the broad range of possibilities, the redox active groups which may be attached to carbon include aromatic quinones, aromatic nitro compounds and metallocenes all of which have previously been disclosed for use in electrochemical sensors.

DETAILED DESCRIPTION

The first stage in derivization of carbon by the process disclosed herein is the attachment of a compound which contains an azo group which will be decomposed in a subsequent step. Such a compound may be represented by a general formula where the groups $R_1$ and $R_2$ are aromatic groups and one of them may also carry a functional group for attachment carbon. Thus the compound may be represented by a formula where X is a functional group. One possibility is that X is a diazonium group and a specific possibility is that the compound is 2,5-dimethoxy-4-([4-nitrophenyl]azo)benzenediazonium chloride which is the commercially available dyestuff fast black K. The attachment of such a compound to elemental carbon, by decomposition of the diazonium group has been documented in the literature, notably in a review by Downard at Electroanalysis vol 12 pages 1085-96 (2000). The scheme of the reaction is

Elemental carbon to which an azo compound is attached may have a variety of forms including graphite powder, glassy carbon, carbon fibres, carbon black or carbon paste, boron doped diamond and carbon epoxy. A further form of carbon which may be derivatized is the carbon nanotube (CNT) which was discovered in 1991. The structure of carbon nanotubes approximates to rolled-up sheets of graphite and can be formed as either single or multi-walled tubes. Single-walled carbon nanotubes (SWCNTs) constitute a single, hollow graphite tube. Multi-walled carbon nanotubes (MWCNTs) on the other hand consist of several concentric tubes fitted one inside the other. Yet another form of carbon which may be derivatized is graphene which may be in the form of graphene flakes and after derivatization these may be immobilized on a conductive substrate. All of these forms of carbon are carbon in a solid form, which may be a particulate solid, or comprise carbon in a solid form.

The elemental carbon may be conductive and may be for use in an electrode. Forms of conducting carbon used in electrode manufacture are glassy carbon, carbon fibres, carbon black, various forms of graphite, carbon paste, boron doped diamond and carbon epoxy. Carbon nanotubes may also be used as part of an electrode and may be immobilized on the surface of another form of conducting carbon.

Another approach begins by reaction of elemental carbon to introduce functional groups. One possibility is to treat the elemental carbon with strong oxidizing acid, for instance by placing the carbon in a solution containing a mixture of $H_2SO_4$ (3M) and $HNO_3$ (1M) for a period of 24 hours as described by Liu et al Science vol 280 page 1253 (1998). This treatment produces surface bound carboxylic acid groups at the edge plane defects of the elemental carbon surface. Carbon which has been modified with acidic groups can then be reacted with an azo compound of general formula where $X_2$ is a functional group which may be an amino group which becomes converted to an amide on reaction with an acidic group on the elemental carbon. One specific possibility is reaction with phenylazoanilene, thus:

A further approach for attaching an azo compound to elemental carbon is shown below. This begins by reacting the elemental carbon with 4-Benzoylamino-2,5-dimethoxy-benzenediazonium chloride which is the dye "fast blue RR salt" in the same manner as for attachment of fast black K above. The resulting derivatised carbon is then heated to break the amide linkage resulting in the formation of 1,4-dimethoxyaniline derivatised carbon. This newly formed derivatised carbon is then reacted with an azo compound having a carboxylic acid group such as 5-(4-nitrophenylazo) salicylic acid which is the dye alizarin yellow R, also termed Mordant Orange 1.

Decomposition of an azo compound which has been attached to elemental carbon may be brought about with ultraviolet light, heat (which may be supplied as microwave energy) or energy supplied as ultrasound. The decomposition is brought about in the presence of an olefinic compound which can react with the radicals generated by decomposition at the azo group.

Possible olefinic compounds include vinyl ferrocene, vinyl anthracene and vinylanthraquinone. These can be incorporated into a polymer chain extending from the residue of the decomposed azo compound attached to elemental carbon as illustrated by the following scheme in which a poly(vinylferrocene) chain attached to carbon is created:

The procedures discussed above can be used to provide polymer chains which incorporate redox active groups and are attached to elemental carbon, which may be in a particulate form. The particulate carbon may be immobilized on an electrode and used in electrochemistry. Such an electrode may be used in an electrochemical sensor.

Elaborating further on the nature and function of redox-active groups which may be included in a polymer chain and thereby immobilized on an electrode, there are a number of redox active groups which are sensitive to pH, so that when observed by voltammetry, the voltage at which there is maximum current flow (ie the voltage of the peak of the voltammetric wave) is dependent on pH. An electrode with such a group attached to it can be used as a pH sensor.

Aromatic quinones which have such redox reactions are disclosed in WO2005/066618. The use of aromatic nitrogen compounds, which undergo irreversible reduction to hydroxylamine and thereafter undergo pH dependent reversible oxidation from hydroxylamine to nitroso compounds are disclosed in WO2010/001082.

In contrast, the oxidative and reductive peaks for ferrocene are substantially independent of applied voltage, so an electrode with a ferrocene group immobilised on it can serve as a reference when measuring pH, as mentioned in WO2005/066618.

An electrochemical reaction of a redox active group may couple to a reaction of an analyte species of interest and act as a catalyst for its reaction. This analyte species can be determined by means of an amperometric measurement to measure any increase in the electric current which flows when the species is present: the magnitude of the increase in current provides a measure of the concentration of the species of interest.

One instance of this is determination of oxygen. If oxygen is present in an aqueous electrolyte, the electrochemical reduction of a quinone can couple to the reduction of that oxygen to water. The quinone then serves as a catalyst in the electrochemical reduction of oxygen and the concentration of oxygen can be determined from the increase in electric current compared with the current which flows in the absence of oxygen. The reactions can be represented as $$AQ+2H_2O+2e^- \rightarrow AQH_2+2OH^-$$

$$AQH_2+\tfrac{1}{2}O_2 \rightarrow AQ+H_2O$$

Under alkaline conditions, oxygen can be converted to hydrogen peroxide, the second step of the above reaction scheme then becoming:

$$AQH_2+O_2 \rightarrow AQ+H_2O_2$$

If the electrochemical sensor is in contact with a non-aqueous liquid such as acetonitrile, the electrochemical reduction of a quinone can again couple to the reduction of oxygen, but the oxygen is reduced to superoxide, thus:

$$AQ+e^- \rightarrow AQ.^-$$

$$AQ.^- +O_2 \rightarrow AQ+O_2.^-$$

The redox reaction of ferrocene can couple to the oxidation of hydrogen sulphide to sulphur, so that the concentration of hydrogen sulphide can be determined from the increase in current compared to the current which flows in the absence of hydrogen sulphide. The use of ferrocene in the determination of hydrogen sulfide has been mentioned in WO2004/063743 and WO2010/001082. The reactions can be written as $$Fc \rightarrow Fc.^+ +e^-$$

$$Fc.^+ +HS^- \rightleftharpoons Fc+S+H^+$$

Ferrocene compounds can also be used in the determination of other analytes, as mentioned by Lawrence in Electroanalysis vol 18 pp 1658-1663 (2006).

Thus, electrodes carrying carbon to which polymer chains have been attached, where the polymer chains include quinone groups, or include ferrocene groups, can be used as electrochemical sensors. Measurement of pH may be carried out using polymer chains which include a quinone. Polymer chains which include ferrocene groups may serve as a reference and it is possible that a polymer chain could be copolymeric, incorporating both quinone and ferrocene groups.

Electrodes carrying carbon to which are attached polymer chains containing ferrocene groups may be used for measurement of H$_2$S or thiols, in analogous manner to use of ferrocene in documents above.

Particulate carbon may be deposited on an electrode surface, for instance by evaporation of a suspension of the particles in a volatile solvent. Another possibility is to pack such derivatized particulate carbon into a recessed cavity in an electrode. The empty recess might be filled with the derivatized carbon powder which would be mechanically compacted. The resulting void in the recess would then be refilled and compacted again. This would be repeated several times until the recess is full. The material would be pressed such that the carbon particles are packed into a dense matrix.

A further possibility is that derivatized carbon particles may be screen printed onto a substrate which may be an insulating material. Carbon particles derivatized with a second redox active compound which is insensitive to analyte/pH and which acts as a reference may be screen printed onto the same or another substrate. The particulate carbon may be combined with a binding material, which may be a conductive binding material such as a graphite-containing ink, and then screen printed onto the electrode.

An external reference electrode may possibly be used with such a screen-printed electrode. One possible external reference is a silver/silver-chloride electrode. A screen-printed electrode may possibly carry such an external reference electrode on a portion of an insulating substrate. Particulate carbon derivatized with a redox active compound, mixed with a binder may also be applied to a working electrode by an inkjet-type process as an alternative to screen printing.

A screen-printed electrode may possibly be covered with a polymer film or coating. The polymer film or coating may, among other things, make the electrode more robust, prevent external adverse effects of the redox active compound(s), and allow for sterilization of the electrode without affecting the functionality of the electrode.

Some embodiments of electrochemical sensor include a temperature probe for measuring a temperature of the fluid, wherein the temperature measurement may be used to calibrate the electrochemical sensor.

An electrochemical sensor could be incorporated into a wide variety of tools and equipment. Possibilities include use in tools which are located permanently downhole, use in tools which are conveyed downhole, for instance at the head of coiled tubing or by drillpipe or on a wireline, use in underground, undersea or surface pipeline equipment to monitor liquid flowing in the pipeline, and use in a wide variety of process plant at the Earth's surface, including use in water treatment.

Figure 1:
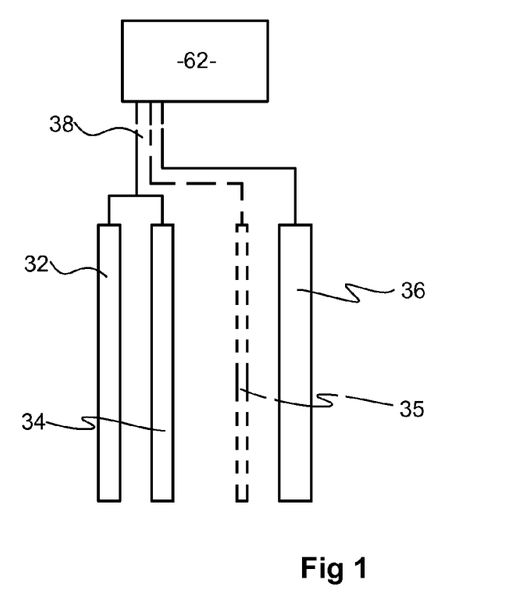
FIG. 1 is a diagrammatic illustration of the parts of an electrochemical sensor.

FIG. 1 diagrammatically illustrates apparatus which may be used in pH measurement. A working electrode 32 has carbon particles with polymer chains incorporating a pH-sensitive redox active groups such as anthaquinone groups attached to the surface of the carbon particles. A reference electrode 34 has carbon particles with polymer chains incorporating a ferrocene compound attached to the surface of the carbon particles. There is also counter electrode 36. All the electrodes are connected by cable or other wiring indicated at 38 to a potentiostat 62 or other control unit which provides electric power and measurement. This arrangement avoids a need for a standard reference electrode such as a standard calomel electrode. However, another possibility would be to provide such a standard electrode, as shown by broken lines at 35 and possibly dispense with the electrode 34 using ferrocene groups. The various electrodes are immersed in or otherwise exposed to fluid whose pH is to be measured.

Measuring apparatus may comprise electrode(s) which utilize derivatized graphite and also a control unit providing both electrical power and measurement. A control unit such as 62 may comprise a power supply, voltage supply, potentiostat and/or the like for applying an electrical potential to the working electrode 32 and a detector, such as a voltmeter, a potentiometer, ammeter, resistometer or a circuit for measuring voltage and/or current and converting to a digital output, for measuring a potential between the working electrode 32 and the counter electrode 36 and/or potential between the working electrode 32 and the reference electrode 34 or 35 and for measuring a current flowing between the working electrode 32 and the counter electrode 36 (where the current flow will change as a result of the oxidation/reduction of a redox species). The control unit may in particular be a potentiostat. Suitable potentiostats are available from Eco Chemie B V, Utrecht, Netherlands.

A control unit 62 which is a potentiostat may sweep a voltage difference across the electrodes and carry out voltammetry so that, for example, linear sweep voltammetry, cyclic voltammetry, or square wave voltammetry may be used to obtain measurements of the analyte using the electrochemical sensor. The control unit 62 may include signal processing electronics.

Figure 2:
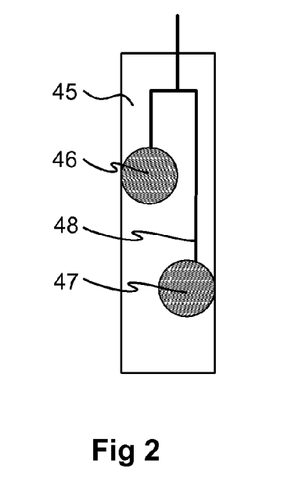
FIG. 2 shows another electrode construction.

FIG. 2 shows a possible variation. A conductive paste containing carbon particles with polymer chains incorporating pH sensitive redox groups is printed on one area 46 of an insulating substrate 45 to provide an electrode 32. A second conductive paste containing carbon particles with polymer chains incorporating pH insensitive ferrocene groups is printed on an area 47 as a reference electrode. The two areas 46, 47 are connected together and connected to a cable 38 leading to a control unit by conductive tracks 48 on the substrate 45.

The electrodes 46, 47 may be screen printed using stencil designs to delineate the areas of the electrode. To form the working electrode, the derivatized carbon particles may be mixed within a carbon-graphite ink and deposited on area 46 of a substrate 45 which may comprise polyester or other insulating polymer. To form the reference electrode a carbon-graphite ink may be deposited on area 47 of the substrate, then a reference electrode material, such as silver/silver-chloride may be deposited as a paste onto the area of deposited carbon. In some embodiments of electrode, a polymer coating may be applied on top of deposited materials (including deposited derivatized carbon). A polymer coating which is permeable to water and other small molecules may prevent derivatized carbon particles from becoming detached from the working electrode, but still allow for interactions between an analyte and redox active groups on the working electrode. For example a polymer coating may comprise a polysulphone polymer or a polystyrene polymer.

Figure 3:
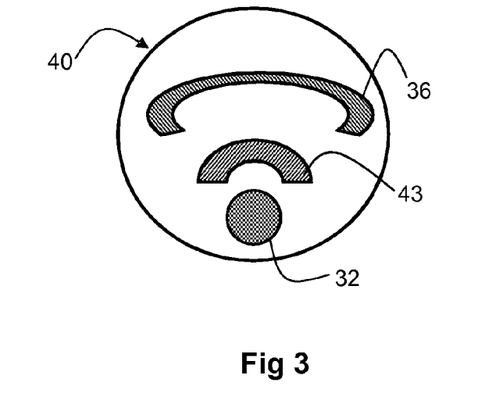
FIG. 3 illustrates the geometrical surface layout of the surface of a sensor.

FIG. 3 shows a possible geometric configuration or layout for the surface 40 of a sensor which is exposed to the fluid to be tested, which may, merely by way of example be a wellbore fluid. The surface includes a disk shaped working electrode 32, a second electrode 43, which may be a electrode using ferrocene groups or an external reference electrode such as a silver/silver chloride electrode, and a counter electrode 36.

Figure 4:
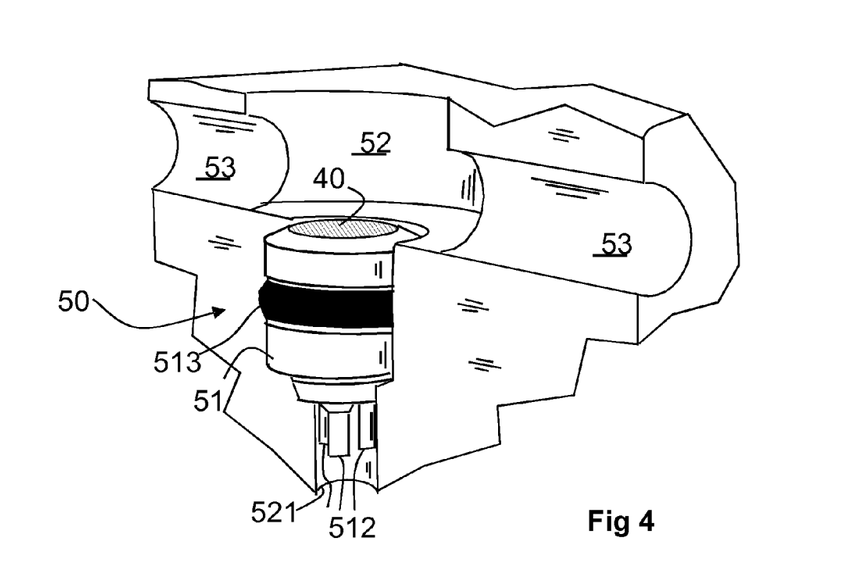
FIG. 4 is a perspective view, partially cut-away, of an electrochemical sensor incorporating the surface of FIG. 3.

A schematic of a microsensor 50 incorporating such a surface is shown in FIG. 4. The body 51 of the sensor is fixed into the end section of an opening 52. The body carries the electrode surface 511 and contacts 512 that provide connection points to voltage supply and measurement through a small channel 521 at the bottom of the opening 52. A sealing ring 513 protects the contact points and electronics from the fluid to be tested that passes under operation conditions through the sample channel 53.

Figure 5:
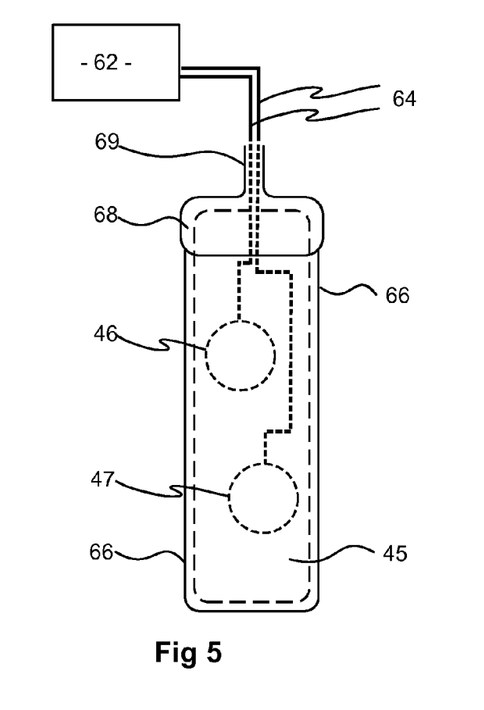
FIG. 5 illustrates a working electrode covered at least in part by a polymer layer.

FIG. 5 shows a substrate 45 carrying a working electrode on an area 46 and a reference electrode on an area 47. These are not connected together but are connected by separate conductors within a cable 64 to a potentiostat 62 which may be a handheld device. After deposition of electrode materials onto the substrate 45, the substrate and deposited materials were coated with a permeable polymer layer indicated by reference 66. Methods to deposit the polymer in a generally uniform layer include spin coating, dip coating and application using solvent evaporation. One end of the coated substrate has an impermeable covering 68 which merges with the sheath 69 of the cable 64.

Figure 6:
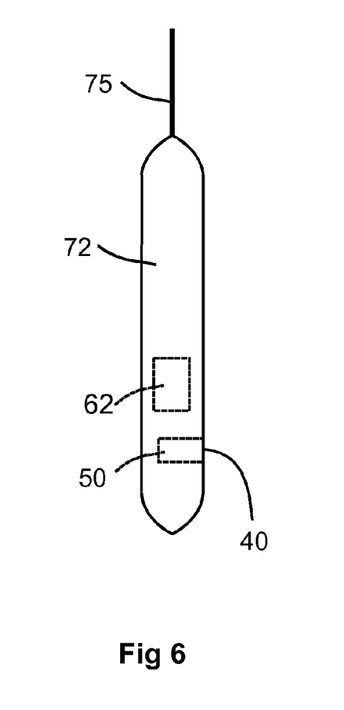
FIG. 6 is a diagrammatic illustration of a cable-suspended tool for testing water.

One application of an electrochemical sensor may lie in the monitoring of underground bodies of water for the purposes of resource management. Using monitoring wells drilled into the aquifers, one or more sensors may be deployed on a cable from the surface. The sensor(s) may be in place for a relatively short duration (as part of a logging operation) or a longer term (as part of a monitoring application). FIG. 6 illustrates a tool for investigating subterranean water. This tool has a cylindrical enclosure 72 which is suspended from a cable 75. A sensor unit such as the sensor 50 shown in FIG. 4 is accommodated within the enclosure 72 so that its surface 40 is exposed to the subterranean water. The tool also encloses also encloses a unit 62 for supplying voltage to the electrodes of the sensor 50, measuring the current which flows and transmitting the results to the surface.

The sensor may be a pH sensor. Suspending such a device on a cable within producing wells may provide information on produced water quality. Also, the pH sensor may be deployed in injection wells, e.g. when water is injected into an aquifer for later retrieval, where pH may be used to monitor the quality of the water being injected or retrieved.

Figure 7:
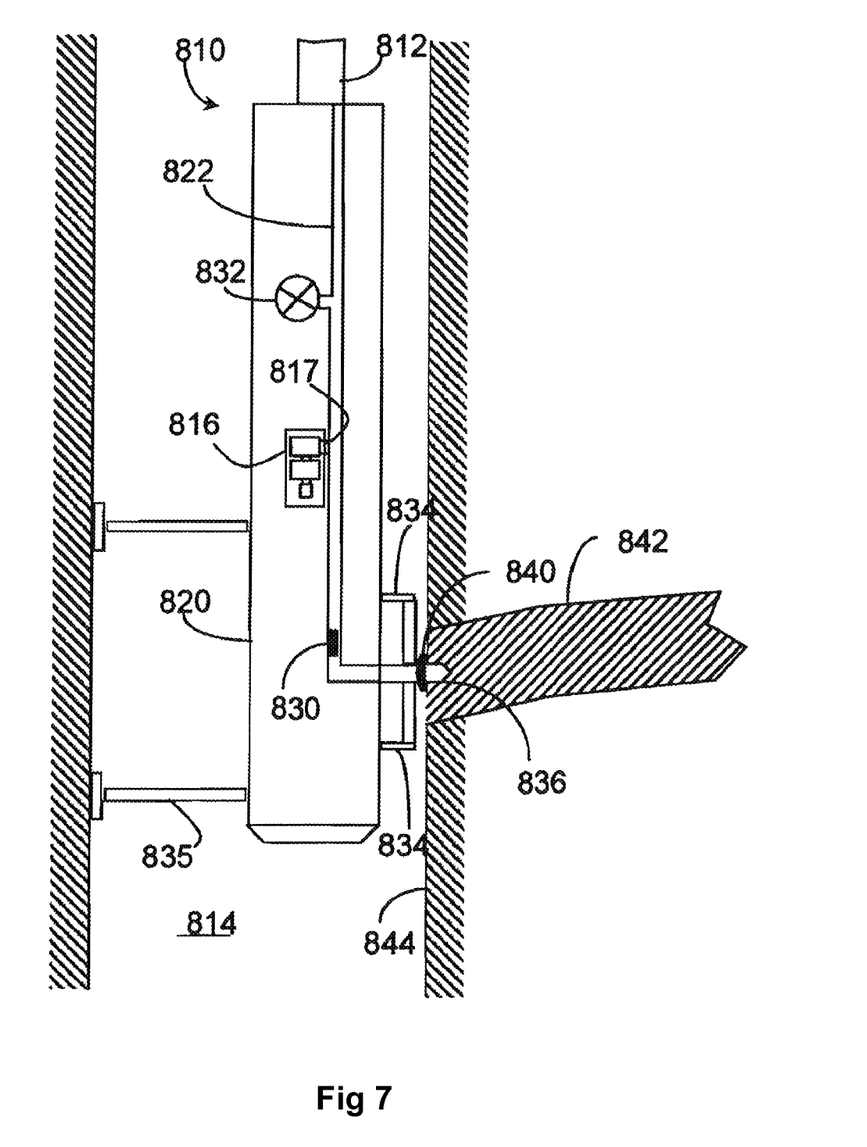
FIG. 7 illustrates an example of an electrochemical sensor, as part of a wireline formation testing apparatus in a wellbore.

FIG. 7 shows a formation testing apparatus 810 held on a wireline 812 within a wellbore 814. The apparatus 810 is a well-known modular dynamic tester (MDT, Trade Mark of Schlumberger) as described in the co-owned U.S. Pat. No. 3,859,851 to Urbanosky, U.S. Pat. No. 3,780,575 to Urbanosky and U.S. Pat. No. 4,994,671 to Safinya et al., with this known tester being modified by introduction of an electrochemical analyzing sensor 816 substantially similar to sensor 50 of FIG. 4 The modular dynamics tester comprises body 820 approximately 30 m long and containing a main flowline bus or conduit 822. The analysing tool 816 communicates with the flowline 822 via opening 817. In addition to the novel sensor system 816, the testing apparatus comprises an optical fluid analyser 830 within the lower part of the flowline 822. The flow through the flowline 822 is driven by means of a pump 832 located towards the upper end of the flowline 822. Hydraulic arms 834 and counterarms 835 are attached external to the body 820 and carry a sample probe tip 836 for sampling fluid. The base of the probing tip 836 is isolated from the wellbore 814 by an o-ring 840, or other sealing devices, e.g. packers.

Before completion of a well, the modular dynamics tester is lowered into the well on the wireline 812. After reaching a target depth, i.e., the layer 842 of the formation which is to be sampled, the hydraulic arms 834 are extended to engage the sample probe tip 836 with the formation. The o-ring 840 at the base of the sample probe 836 forms a seal between the side of the wellbore 844 and the formation 842 into which the probe 836 is inserted and prevents the sample probe 836 from acquiring fluid directly from the borehole 814.

Once the sample probe 836 is inserted into the formation 842, an electrical signal is passed down the wireline 812 from the surface so as to start the pump 832 and the sensor systems 816 and 830 to begin sampling of a sample of fluid from the formation 842. The electrochemical sensor 816 can then measure the pH or concentration of another analyte such as hydrogen sulfide in the formation effluent.

While the preceding uses of an electrochemical sensor are in the hydrocarbon and water industries, embodiments of electrochemical sensor incorporating derivatized carbon may be used for detecting an analyte in a whole host of industries, including food processing, pharmaceutical, medical, water management and treatment, and biochemical industries, as well as research laboratories. A polymer coating may prevent escape of derivatized carbon particles from an electrode into the fluid around it, but still allow for interactions between an analyte and one or more redox active compounds on the electrode.

It will be appreciated that the example embodiments described in detail above can be modified and varied within the scope of the concepts which they exemplify. Features referred to above or shown in individual embodiments above may be used together in any combination as well as those which have been shown and described specifically. Accordingly, all such modifications are intended to be included within the scope defined in the following claims.

The invention claimed is:

1. A process for chemical modification of the surface of elemental carbon comprising attaching a compound which contains an azo group and which has a formula $$R_1-N=N-R_2$$

where the groups $R_1$ and $R_2$ are aromatic groups, to the elemental carbon so as to provide groups of the formula $$-N=N-R_2$$

attached to the carbon surface through linking groups each of which contains at least part of $R_1$ and which are attached to the carbon surface, and then decomposing the azo group in the presence of one or more further compounds which contain an olefinic group so that decomposition of the azo group forms radicals and a said radical forms a covalent bond to a said olefinic group, so that the one or more further compounds become attached to the elemental carbon through the linking groups.

2. A process according to claim 1 wherein the compound which contains an azo group has a formula $$X-R_1-N=N-R_2$$

where the groups $R_1$ and $R_2$ are aromatic groups and X is a diazonium group.

3. A process according to claim 1 wherein a said further compound which contains an olefinic group comprises vinylferrocene.

4. A process according to claim 1 wherein a said further compound which contains an olefinic group comprises vinylanthracene or vinylanthraquinone.

5. A process according to claim 1 wherein the elemental carbon is in particulate form and the process further comprises immobilizing the elemental carbon modified by the attachment of one or more said further compounds on an electrode.

6. A process according to claim 1 which comprises attaching functional moieties to the surface of the elemental carbon and then attaching the compound which contains an azo group, wherein the compound which contains an azo group has a formula $$X_2-R_1-N=N-R_2$$

where the groups $R_1$ and $R_2$ are aromatic groups and $X_2$ is a functional group which is able to combine with the functional moieties attached to the elemental carbon.

7. A process according to claim 1 wherein a said further compound which contains an olefinic group comprises a vinyl compound having the general formula $R_3-CH=CH_2$, wherein $R_3$ is a group capable of redox reaction in aqueous solution.

8. A process according to claim 1 wherein the elemental carbon is graphite powder or carbon nanotubes.

* * * * *